(12) United States Patent
Hubbell et al.

(10) Patent No.: US 6,752,007 B1
(45) Date of Patent: Jun. 22, 2004

(54) HORIZONTAL ADVANCED TENSIOMETER

(75) Inventors: Joel M. Hubbell, Idaho Falls, ID (US); James B. Sisson, Idaho Falls, ID (US)

(73) Assignee: The United States of America as represented by the United States Department of Energy, Washington, DC (US)

( * ) Notice: Subject to any disclaimer, the term of this patent is extended or adjusted under 35 U.S.C. 154(b) by 0 days.

(21) Appl. No.: 10/215,033

(22) Filed: Aug. 9, 2002

(51) Int. Cl.[7] .................................................. G01L 5/02
(52) U.S. Cl. ............................................. 73/73; 73/826
(58) Field of Search ............................... 73/73, 78, 81, 73/84

(56) References Cited

U.S. PATENT DOCUMENTS

| | | | |
|---|---|---|---|
| 5,644,947 A | 7/1997 | Hubbell et al. | |
| 5,758,538 A | 6/1998 | Hubbell et al. | |
| 5,915,476 A | 6/1999 | Hubbell et al. | |
| 5,941,121 A * | 8/1999 | Faybishenko | 73/73 |
| 6,263,726 B1 | 7/2001 | Hubbell et al. | |
| 6,289,725 B1 | 9/2001 | Hubbell et al. | |
| 6,308,563 B1 | 10/2001 | Hubbell et al. | |
| 6,539,780 B2 * | 4/2003 | Hubbell et al. | 73/73 |

* cited by examiner

*Primary Examiner*—Max Noori
(74) *Attorney, Agent, or Firm*—Brian J. Lally; Daniel D. Park; Paul A. Gottlieb

(57) ABSTRACT

An horizontal advanced tensiometer is described that allows the monitoring of the water pressure of soil positions, particularly beneath objects or materials that inhibit the use of previous monitoring wells. The tensiometer includes a porous cup, a pressure transducer (with an attached gasket device), an adaptive chamber, at least one outer guide tube which allows access to the desired horizontal position, a transducer wire, a data logger and preferably an inner guide tube and a specialized joint which provides pressure on the inner guide tube to maintain the seal between the gasket of the transducer and the adaptive chamber.

21 Claims, 7 Drawing Sheets

HORIZONTAL ADVANCED TENSIOMETER

U.S. GOVERNMENT RIGHTS

The United States Government has rights in this invention pursuant to Contract No. DE-AC07-99ID13727 between the U.S. Department of Energy and BECHTEL BWXT IDAHO, LLC, representing Idaho National Engineering & Environmental Laboratory.

TECHNICAL FIELD

The invention relates to an apparatus for the monitoring of groundwater for environmental investigations. More specifically, the invention is a horizontal advanced tensiometer which measures the "soil water potential" (how well surrounding soil and rock hold water) of soil and rock positions beneath objects or overlying material.

BACKGROUND OF THE INVENTION

Since soil water potential indicates how well surrounding soil and rock holds water, measuring soil water potentials at various locations and depths allows scientists to understand how fluids move between the land surface and the water table below. Understanding how fluids travel through the soil is an important aspect of environmental studies and is very helpful in developing improved irrigation management. Traditionally, tensiometers have been the instruments of choice for recording such water potential measurements.

Traditional tensiometers consist of a sealed tube (filled with water) which is connected to a hollow porous tip at one end and a vacuum gauge at the other. The porous tip is then inserted into the soil at the desired monitoring position. As the water content of the surrounding soil decreases so does its water potential relative to that of the water in the tip. The difference in water potential causes the water in the sealed tube to move through the tip pores and into the surrounding soil. Thus, relatively dry soil pulls water through the porous tip and creates a partial vacuum in the tube. The vacuum gauge then records the pressure level of the ambient soil. The more saturated the soil, the less vacuum created, and the lower the pressure recorded.

Many of the problems associated with traditional tensiometers were solved with the development of advanced tensiometers. Advanced tensiometers utilize electronic pressure transducers mounted at the point of measurement which eliminate the need for the long water columns taught by traditional tensiometer designs. See, Hubbell et al., U.S. Pat. No. 5,915,476.

Although advanced tensiometer designs have solved the problem of water column length, previous tensiometer designs have failed to solve problems associated with monitoring soil conditions in areas beneath objects or material. Previous tensiometer designs have difficulty in measuring such areas because they employ vertical monitoring wells that are inefficient or ineffective in monitoring soil which lies beneath buildings or other structures or material.

There remains a need for horizontal monitoring of soil moisture potentials in areas beneath objects where vertical monitoring devices would be inefficient or ineffective.

OBJECTS OF THE INVENTION

An object of the invention is to provide an apparatus to measure soil water potential beneath the earth's surface.

Another object of the invention is to provide an apparatus to measure soil water potential in horizontal layers beneath objects or overlying material.

Another object of the invention is to provide a means of maintaining the seal between the transducer and the adapter to ensure accurate measurements.

BRIEF DESCRIPTION OF THE DRAWINGS

Preferred embodiments of the invention are described below with references to the following accompanying drawings.

DETAILED DESCRIPTION OF THE PREFERRED EMBODIMENTS

The present invention is an apparatus for measuring soil water potentials. More specifically, the invention facilitates the monitoring of soil water potentials at certain hard to reach soil positions by providing an apparatus that can be positioned in areas beneath objects or overlying material that could not be effectively monitored using previous designs. There are three related embodiments of the present invention. All three of the embodiments utilize the same core elements but differences exist to allow for the different orientations they represent.

First Embodiment

A monitoring well is formed by drilling a borehole 22, using horizontal drilling or guided boring techniques, into the ground of the area to be monitored. (see, FIG. 1.) The top of the borehole 22 is drilled at an off-horizontal angle relative to the land surface 4. The middle of the bore hole 22 should curve until it is approximately horizontal with the land surface 4 above. The end portion of the borehole should be drilled at an approximately horizontal orientation relative to the land surface 4, terminating at the desired monitoring position. (see, FIG. 1)

Figure 1:
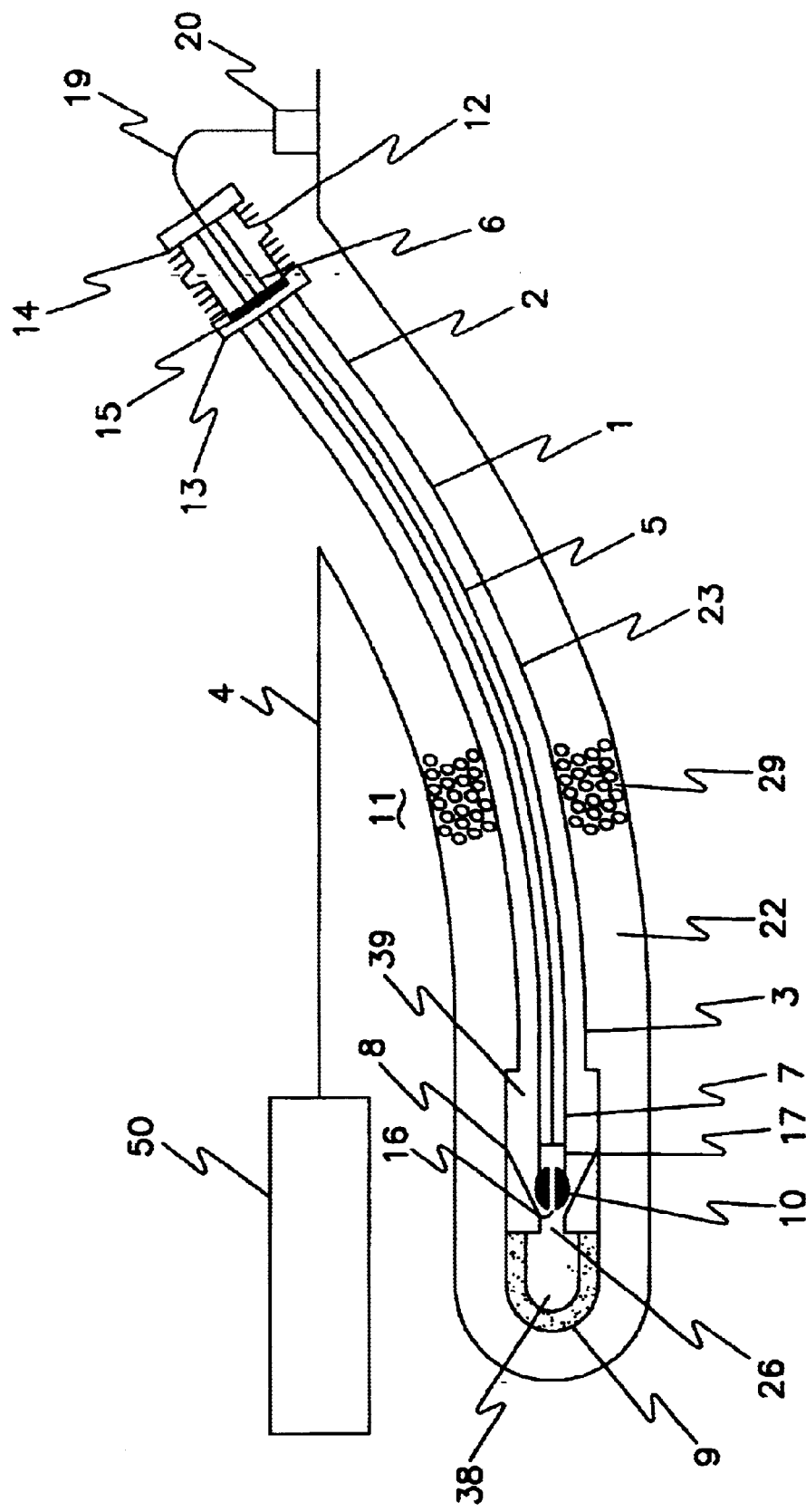
FIG. 1 is an elevational sectional view of the first embodiment of present invention.

FIG. 1 shows a schematic view of the first embodiment of the horizontal advanced tensiometer. The first embodiment consists of an outer guide tube 1 that acts as an exterior support for the tensiometer. The outer guide tube 1 can be constructed of any material suitable for groundwater wells and which is flexible enough to bend without compromising the structural integrity of the tube, such as PVC, ABS, or steel pipe. The guide tube 1 (along with the porous cup and adapter discussed later) is inserted into the pre-drilled bore hole 22. (see FIG. 1) When the outer guide tube 1 is in position, it has an a upper straight end 2, a curved middle section 23, and a lower straight end 3. (see, FIG. 1) The upper end of the guide tube 2 is oriented at an off-horizontal angle in relation to the land surface 4. The outer guide tube 1 extends from above the land surface 4 to below land surface at the desired monitoring elevation. The middle curved section 23 bends the guide tube from an off-horizontal angle relative to the land surface to an approximately horizontal angle (approximately parallel) relative to the land surface 4. The lower end of the guide tube 3 is approximately horizontal in relation to the land surface 4 and allows monitoring of positions under objects or material 50. Fill material 29 such as sand, gravel, bentonite, etc., is placed in the borehole 22 around the outer guide tube 1 to secure the guide tube within the surrounding earthen material. (see, FIG. 1)

The lower end of the guide tube 3 (see, FIG. 1) is connected to the first end of an adaptor 8 using a water proof adhesive, or other suitable coupling device or material, to form a water tight seal. It is important that when a water tight seal is called for in this specification that such a seal is formed. If a water tight seal is not formed water could leak out of the apparatus and affect the accuracy of the readings.

The second end of the adaptor 8 (see, FIG. 1) is connected to a porous cup 9 using a water proof adhesive, or other suitable coupling device or material, to form a water tight seal. The porous cup 9 is made of a porous ceramic, a porous plastic, or a specialized stainless steel, etc., which is known in the art. In this case, the specialized porous stainless steel is, Stainless Steel 316 (pore size 0.2 micron), produced by Mott Metallurgical Corporation, Farmington, Conn. 06032. The ceramic is a ceramic produced by Soil Moisture Equipment Corp., (2 bar ceramic) Santa Barbara, Calif. 93105 or similar ceramic. The porous cup 9 has an outer surface which is in contact with the outside soil 11 and an inner surface which defines a chamber 38. (see, FIG. 1) The pores in the material forming the cup allow water to move between the inner chamber of the cup 38 and the surrounding soil 11. The amount of water that travels through the pores depends on the water potential pressure differential between the cup's chamber 38 and that of the surrounding soil 11.

Figure 2:
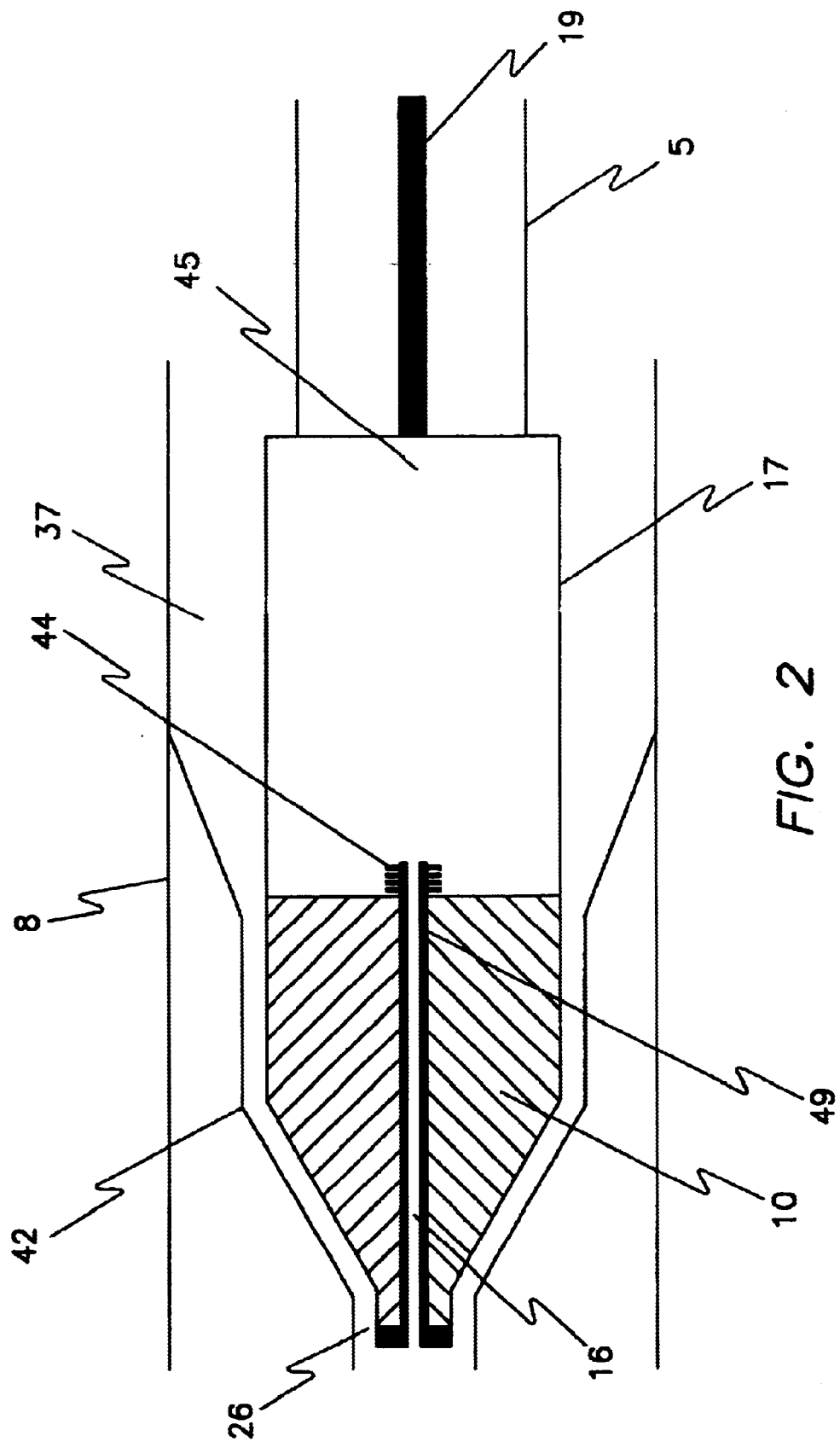
FIG. 2 is a fragmentary elevational sectional view of the adapter of embodiments 1 and 2 of the present invention.

The adapter 8 (see, FIG. 2) has a central open chamber 37 which terminates in an inner conically tapered seat 42 leading to a central aperture 26. The aperture 26 leads to the interior of the porous cup 38 and allows for water to flow between the chamber of the adapter 37 and the chamber of the porous cup 38. (see, FIG. 1)

The first embodiment further consists of a coaxial inner guide tube 5 (see, FIG. 1) positioned within the outer guide tube 1. The inner guide tube 5 can be constructed of flexible tubing which is flexible enough to slip through the bend in the outer guide tube 1. The inner guide tube 5 has an upper end 6 and a lower end 7.

The lower end of the inner guide tube 7 (see, FIG. 1) is attached to the output end 45 of a pressure transducer 17 by a waterproof adhesive or other coupling device or material. The transducer 17 employed in this case is a model number 15, Gauge Pressure Transducer (± 800 cm) sold by Electronics Engineering Innovations, Las Cruces, N.Mex. 88005. However, a similar pressure transducer can be used. The monitoring end of the transducer 17 is connected to a single hole stopper 10 or similar coupling device or material, forming a water tight seal. (see, FIG. 2) In the present case a stopper retainer 49 was utilized to hold the stopper in place against the transducer 17. The stopper retainer 49 has a threaded end and a flat end. (see, FIG. 2) The threaded end is inserted through the stopper aperture 16 and mated with a complimentary thread drilled into the monitoring end of the transducer 44. The flat end of the stopper retainer 49 supplies pressure on the stopper 10 relative to the degree the stopper retainer 49 is mated with the transducer 17. The stopper retainer 49 has a central aperture which runs its entire length and allows fluid communication between the monitoring end of the transducer 44 and the interior of the porous cup 38. (see, FIG. 2)

The single hole perforated stopper 10 terminates in a conically tapered outer surface complementary to that of the tapered seat 42 of the adapter 8. The single hole stopper 10 can be constructed of any suitable resilient material, such as rubber, neoprene, or silicone. The conical end of the stopper 10 mates with the part of the inner surface of the adapter that corresponds to the single hole stopper's shape 42, forming a water tight seal. (see, FIG. 2)

The stopper 10 (see, FIG. 2) has a central aperture 16 which leads to the aperture of the adaptor 26 on one end and monitoring end of the pressure transducer 17 on the other. The single hole stopper aperture 16 completes a pathway that allows water, air and pressure to travel between the porous cup 38 and the monitoring port 44 of the transducer 17. (see, FIG. 2) This fluid communication allows electronic sensors attached to a diaphragm located at the monitoring port of the transducer 17 to measure (using electronic resistance ) the pressure associated with the water potential differential between the surrounding soil 11 and the water inside the porous cup 9. The transducer 17 sends the information through a transducer wire 19 (connected to the transducer and run through the inner guide tube) to a data logger 20 located above the land surface where the information is recorded. The data logger installation includes a 23× Data Logger sold by Campbell Scientific Electronics, 815 West, 1800 North, Logan Utah 84321 or similar data logging device.

Figure 4:
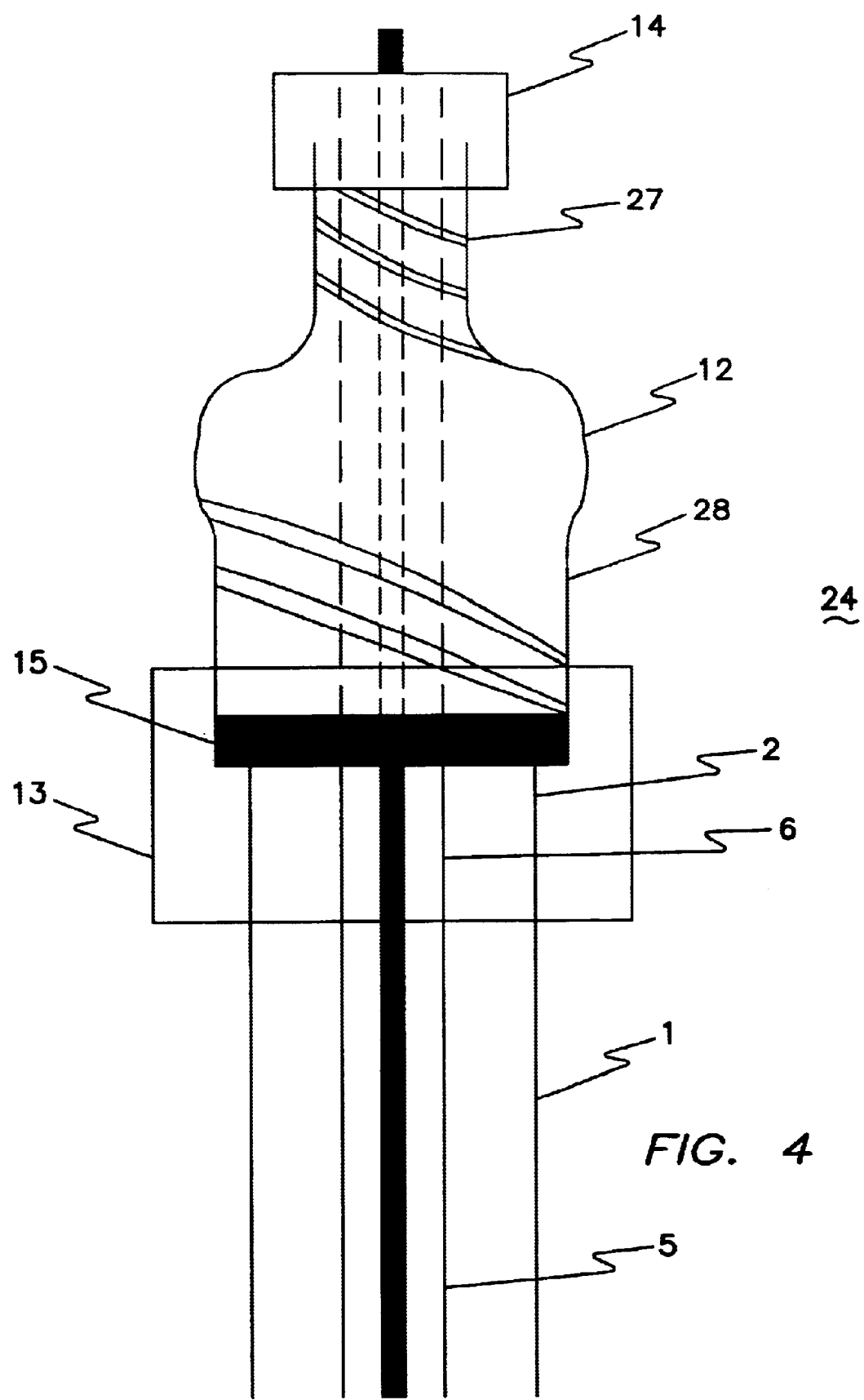
FIG. 4 is a sectional view of the joint of the present invention.

The upper end of the outer guide tube 2 and the upper end of the inner guide tube 6 lead to a joint 24 (see, FIG. 1). The joint 24 is a device that can put a enough pressure on the inner guide tube 5 to maintain the water tight seal between the stopper 10 and the inner surface of the adapter 42. In this case the joint 24 comprises a coupling device 12, rubber gasket 15, lower cap 13 and upper cap 14. (see, FIG. 4) The coupling device 12 is a common plumbing device called a slip joint union adapter, although a similar device can be used. The gasket 15 is fitted snugly over the outside of the upper end of the outer guide tube 2. The gasket 15 has a central aperture which allows the inner guide tube 5 to pass through. The coupling device 12 fits snugly over the gasket 15. The gasket 15 helps the coupling device 12 to fit more securely around the upper portion of outer guide tube 2.

The coupling device 12 has an upper end 27 and a lower end 28. (see, FIG. 4) The coupling device 12 further has a central aperture. The aperture of the coupling device is large enough on the lower end 28 to fit snugly over the gasket 15 and gets progressively smaller until the upper end is only large enough to allow the inner guide tube 5 to pass through. The lower end of the coupling device 28 terminates with threads complimentary to those of the lower cap 13. The upper end of the coupling device 27 terminates with threads complimentary to those of the upper cap 14.

The lower cap 13 has a central aperture large enough to fit around the outside of the outer guide tube 1. (see, FIG. 4) The lower cap 13 further has threads that are complimentary to those of the lower end of the coupling device 28 and which can be mated with the coupling device 12 to form a seal. The lower cap 13 must be fitted over the outer guide tube 2 before the gasket 15 and coupling device 12 are attached. After the gasket 15 and coupling device 12 are attached, the lower cap 13 is mated with the lower end of the coupling device 28 securing the coupling device 12 in place.

The upper cap 14 has a central aperture large enough to allow the transducer wire 19 to pass through but small enough to prevent the inner guide tube 5 to pass through. It is important the upper cap 14 does not allow the inner guide tube 5 from passing through because, as we will see, it allows the cap to apply pressure to the inner guide tube 5. (see, FIG. 4) The upper cap 14 further has threads that are complimentary to those of the upper end of the coupling device 27 and which can be mated with the coupling device to form a seal. The upper cap 14 screws onto the upper part of the coupling device, pressing the inner guide tube 5 with sufficient force to maintain the water tight seal between the stopper 10 and the inner surface of the adapter 42. (see, FIG. 1) Without this applied force the seal between the stopper 10 and the inner surface of the adapter 42 could be compromised, affecting the accuracies of the measurements taken.

The transducer wire 19 runs from the transducer 17, through the inner guide tube 5, up through the coupling device 12, and through the upper cap 14, terminating at a data logger 20 located above the land surface 4. The transducer wire 19 relays the data from the transducer 17 to the data logger 20. (see, FIG. 1)

Method of Use

The method of operation for the first embodiment involves drilling a bore hole 22 as described earlier to the desired location to be monitored. (see, FIG. 1) The porous cup 9, adapter 8 and, outer guide tube 1 are then put into position. Water is poured into the outer guide tube until a sufficient amount has been added to fill the porous cup 9, adaptor 8, and the lower end of the outer guide tube 3. The lower cap 13, gasket 15, and coupling device 12 are then attached to the outer guide tube. (see, FIG. 1) The inner guide tube (with stopper 10 and transducer 17 attached) is then inserted through the coupling device 12 (with upper cap 14 off) and into the outer guide tube 1 until the conical end of the stopper 10 sealingly engages the complimentary conical seat of the adapter 8. (Alternatively, the transducer 17 can inserted before the attachment of the lower cap 13, gasket 15 and coupling device 12). A short length of the inner guide 5 should be left sticking out of the upper end of the coupling device 28. The upper cap 14 is screwed onto the upper part of the blank coupling, pressing down on the inner guide tube 5 with sufficient force to maintain the water tight seal between the stopper 10 and the adapter 8.

The transducer wire 19 is then attached to the data logger and readings can commence. The transducer 17 measures the pressure associated with soil water potential and that information is sent to the data logger 20 where it is recorded and can be later retrieved. The typical data logger installation includes a modem, battery, cellular phone and enclosure to ensure that the data stays protected and to allow the data to be sent to off-site locations. Installations can also include a solar panel for recharging the battery to allow longer operational time.

Second Embodiment

Figure 5:
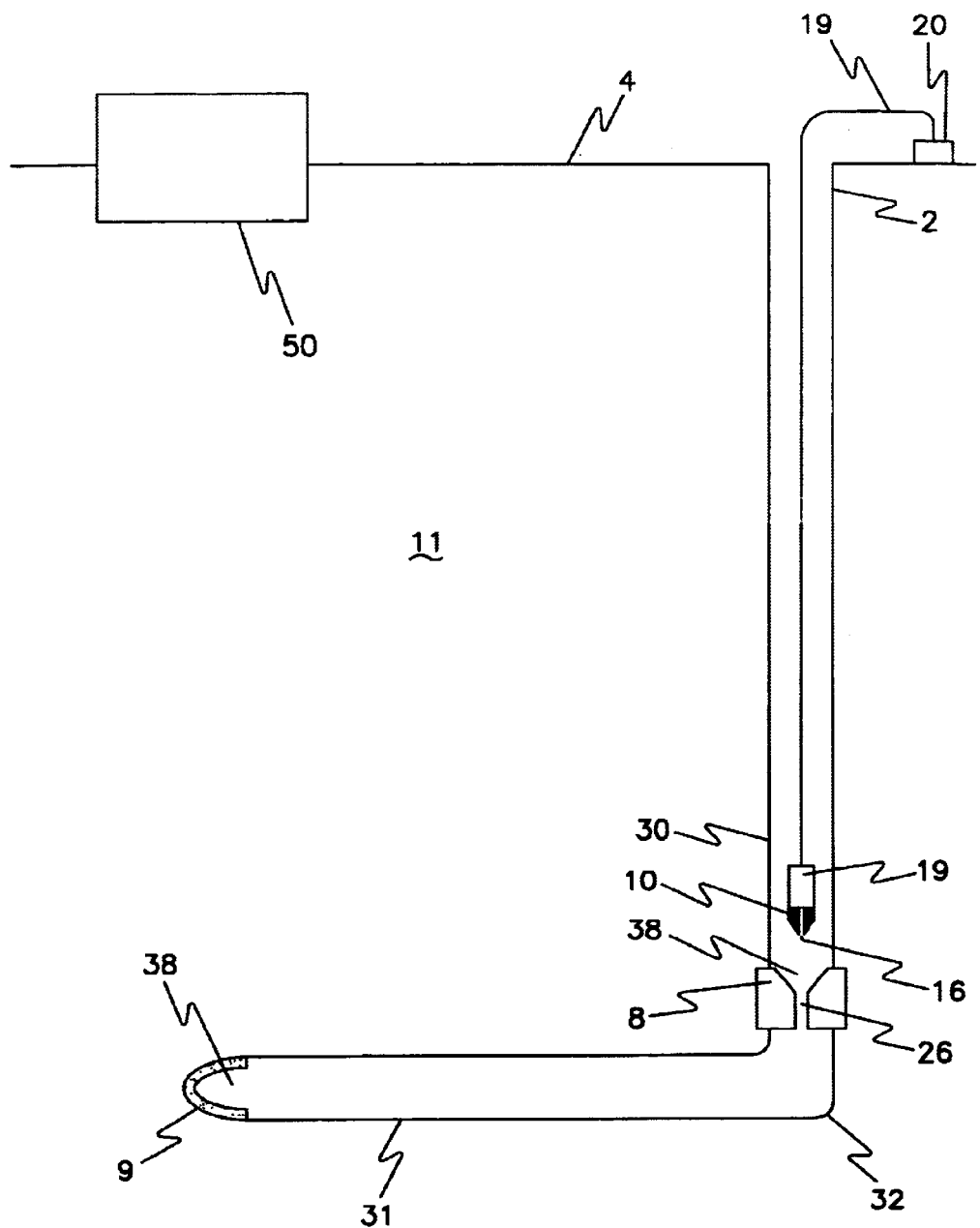
FIG. 5 is an elevational sectional view of the second embodiment of the present invention.

FIG. 5 shows a schematic view of the second embodiment of the horizontal advanced tensiometer. The second embodiment is similar to the first but is slightly modified. The second embodiment uses two outer guide tubes, one horizontal 31 to the land surface and one vertical 30 to the land surface, in place of the single angled outer guide tube 1 described in embodiment 1. (compare FIG. 5 and FIG. 1) The use of two guide tubes allows the transducer 17 to be installed in a vertical manner (while allowing monitoring of horizontal positions) and avoids the complications of passing the transducer 17 through a bend. (see, FIG. 5) This embodiment can be utilized in situations where one can install the tensiometer prior to when the material to be monitored is added. One such example is waste sites.

The use of two guide tubes requires a slight rearrangement of the elements. In the second embodiment a horizontal guide tube 31 is positioned between the porous cup 9 and the adapter 8. (see, FIG. 5) The horizontal guide tube 31 has a straight end and a elbow between 20°–160°. 32. The straight end of the horizontal guide tube 32 is attached to a horizontally oriented porous cup 9 using a waterproof adhesive, or other suitable coupling device or material, to form a water tight seal. (Again, it is important that when a water tight seal is called for in this specification that such a seal is formed. Otherwise, water could leak out and affect the accuracy of the readings.) The porous cup 9 is of the same type and function as the one used in embodiment 1.

The elbow of the guide tube 32 is attached to the lower end of a vertically oriented adapter 8 using a waterproof adhesive, or similar coupling device or material, to form a water tight seal. (see, FIG. 5) The adapter 8 is the same type and performs the same function as the one described in embodiment 1. The aperture of the adapter 26 (FIG. 2) leads to the interior of the elbow of the guide tube 32 (see, FIG. 5) and allows water to flow between the horizontal guide tube 31 and the chamber of the adapter 8. (see FIG. 5)

The first end of the vertical guide tube 30 is attached to the upper end of the adapter 8, by waterproof adhesive or other suitable coupling device or material. (see, FIG. 5) The second end of the vertical guide tube 30 extends to above the land surface 4. The horizontal 30 and vertical 31 guide tubes can be constructed of any material suitable for groundwater wells, such as PVC, ABS or steel pipe.

The second embodiment further consists of a transducer 17 (attached to a single hole stopper 10 on one end and a transducer wire 19 on the other) positioned within the vertical guide tube 30. The transducer 17, single hole perforated stopper 10, transducer wire 19, and data logger 20 are the same type and perform the same function as described in embodiment 1.

The transducer 17 should be of sufficient weight that when the transducer is lowered down the vertical guide tube 30 (using the transducer wire 19 to control the decent), the stopper 10 (attached to the transducer 17) should meet with the complimentary inner surface of the adapter 42 (see, FIG. 2) with sufficient force to form a water tight seal. Weight can be added to the transducer 17 if needed, or the coupling device and inner tubing described in embodiment 1 can be used.

When sealingly engaged with the adapter 8, the perforated stopper aperture 16 (see, FIG. 2) completes a pathway that allows air, water, and pressure to travel between the interior of the porous cup 38 and the monitoring port of the transducer 17. (see, FIG. 5) This fluid communication allows the transducer to measure the pressure created by the water potential differential between the surrounding soil 11 and the water inside the porous cup 9 and horizontal guide tube 31. The horizontal guide tube 31 should be horizontal or slightly angled to allow water to fill the chamber formed by the tube 31. The transducer wire 19 relays the data to the data logger 20.

Method of Use

This method is used when one wants to monitor a position, such as a waste site, that will be filled in the future.

The method of use for the second embodiment involves placing the porous cup 9, adapter 3 and outer horizontal guide tube 31 in the desired position to be monitored. As the waste or other material is deposited above the monitoring position one can add to the length of the vertical outer guide tube 30 so that it remains above land surface 4 level. Tap water is poured into the vertical guide tube 30 until a sufficient amount has been added to fill the porous cup 9, horizontal guide tube 31 and adapter 8. The transducer 17 is then lowered into the vertical guide tube 30 until the conical end of the stopper 10 engages with the complimentary conical seat of the adapter 8 to form a seal. If the seal does not hold, one can add an inner guide tube and joint to the apparatus (see, FIG. 4), as discussed in embodiment 1. The method of data recording is the same as described in embodiment 1.

Third Embodiment

Figure 6A:
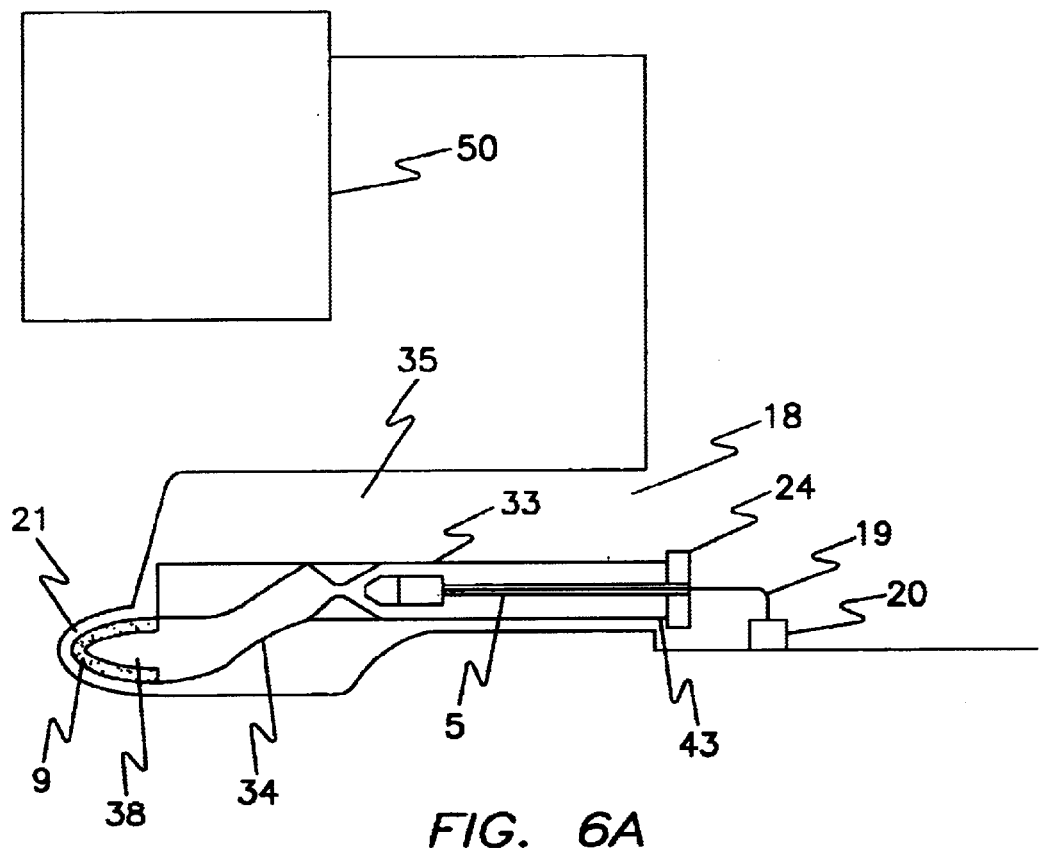
FIG. 6A is an elevational sectional view of the third embodiment of the present invention.
Figure 6B:
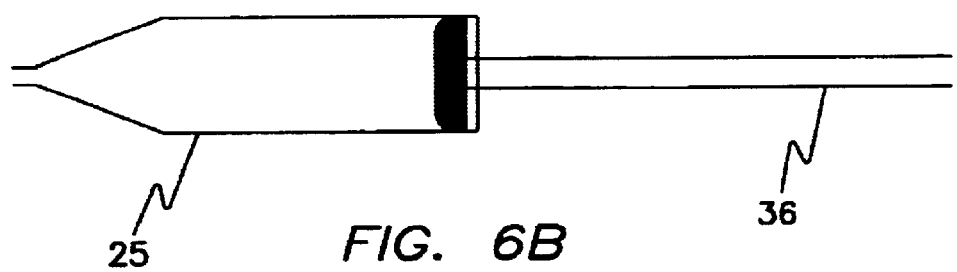
FIG. 6B is a sectional view of the syringe device and rod of the third embodiment of the present invention.

FIG. 6 shows a schematic view of the third embodiment of the horizontal advanced tensiometer. The third embodiment is also similar to embodiment 1 but again has slight modifications. The borehole 35 of embodiment 3 is different because it is drilled into a wall of earthen material as opposed to be being drilled downward from the land surface (compare FIGS. 1 and 6). The borehole 35 has an outer end 18 and an inner end 21. (see, FIG. 6) The borehole 35 is drilled in a near horizontal orientation in relation to the land surface 4. The borehole 35 is angled slightly downward from the outer 18 to inner ends 21 to prevent water from leaking out of the pipe 33 that will be installed. Furthermore, the inner end of the borehole 21 should be dug slightly deeper than the rest of the borehole. This height differential helps keep the water in the porous cup 9 from trickling out of the cup and down the guide pipe 33.

The third embodiment consists of a horizontal guide pipe 33 inserted into the borehole 35. The guide pipe 33 has first end and a second end. The first end of the guide pipe 33 is attached to first end of an adapter 34 using a waterproof adhesive or, other suitable coupling device or material, to form a water tight seal. (Again, it is important that when a water tight seal is called that such a seal is formed. Otherwise water could leak out and affect the accuracy of the readings.) The second end of the guide pipe 33 is connected to a joint 24. (see, FIG. 6)

The second end of the adaptor 34 is connected to a porous cup 9 (the porous cup being placed at the innermost end of the borehole) using a waterproof adhesive, or similar coupling device or material, to form a water tight seal. The porous cup 9 is the same type and has the same function as the one described in Embodiment 1.

Figure 3A:
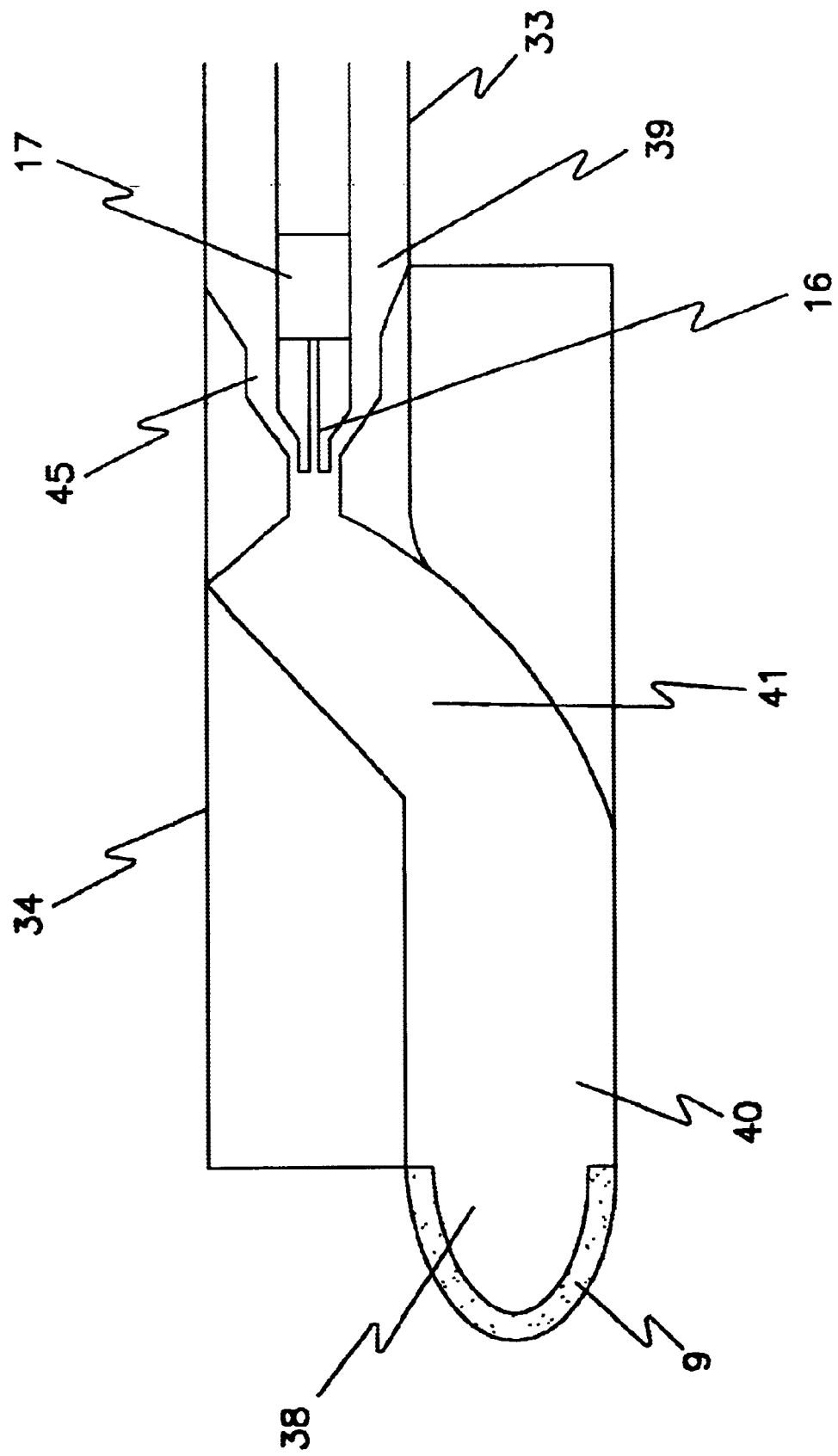
FIG. 3A is a sectional view of the adapter of the third embodiment of the present invention.

The adapter 34 of embodiment 3 is slightly modified to account for the height differential between the porous cup 9 and the outer guide tube 33. (see, FIG. 3A) The adapter 34 has an upper aperture 39 on the side connected to the guide tube 33 and a lower aperture 40 on the side connected to the porous cup 9. (see, FIG. 3A) A passageway 41 connects the lower and upper apertures of the adapter 34. The upper part of the passageway narrows into a conically tapered seat and the lower passageway leads to the interior of the porous cup 38. The passageway 41 allows water to travel between the interior of the porous cup 38 and the guide tube 33. (see, FIG. 3A)

Figure 3B:
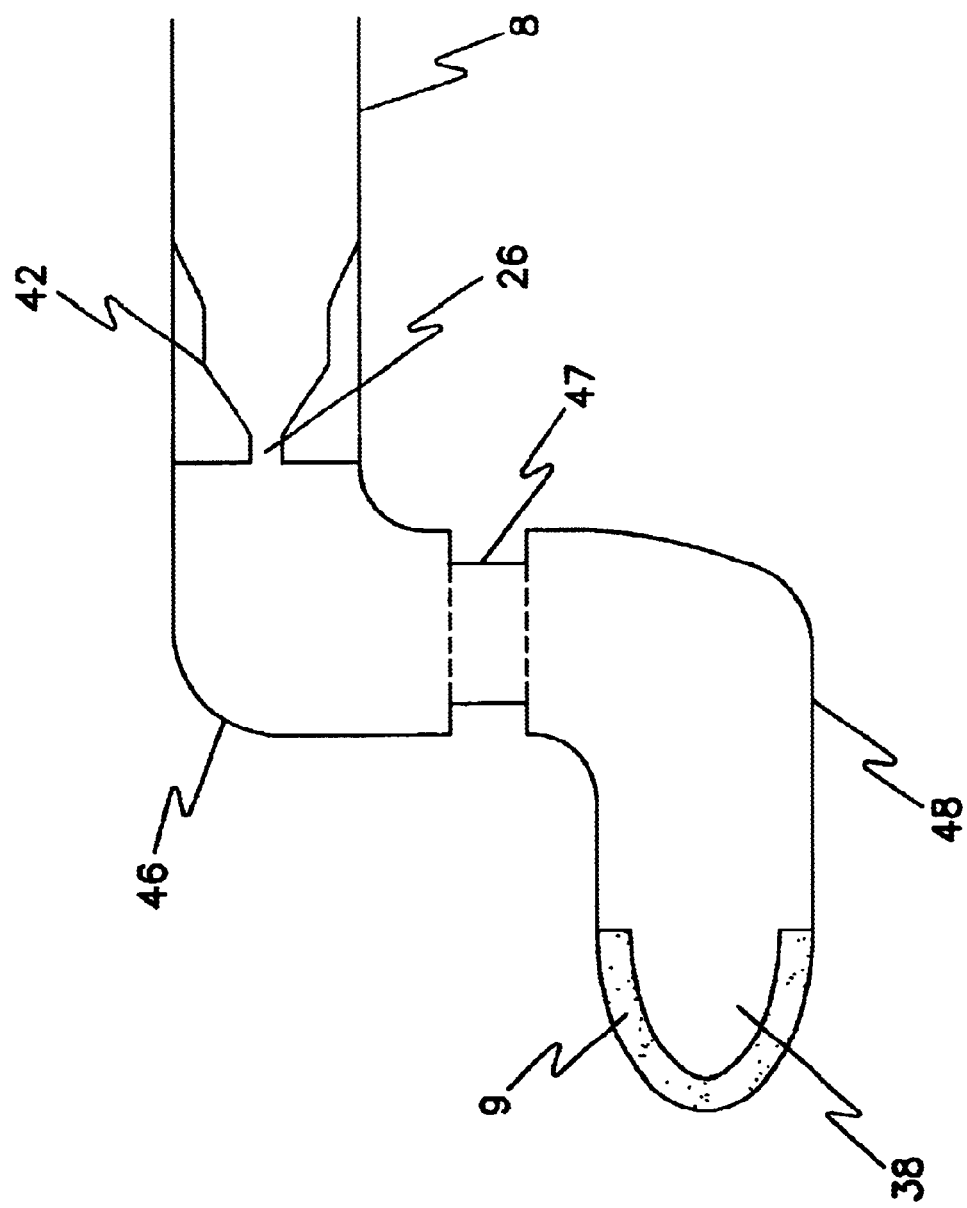
FIG. 3B is a sectional view of the porous cup, the adapter described in embodiments 1 and 2, and a joint allowing use of that adapter in embodiment 3.

Alternatively, the adapter 8 described in embodiments 1 and 2 may be used. (see, FIG. 3B) In this alternative embodiment, the first end of an adapter 8 is attached to the inner end of the outer guide tube 33 using a waterproof adhesive, or other suitable coupling device or material, to form a water tight seal. The second end of the adapter 8 is attached to the first end of an angled coupler 46 using a waterproof adhesive, or other suitable coupling device or material, to form a water tight seal. In this particular case a 90° coupler was used but several different types of angled couplers can be used, including 45° couplers. (see, FIG. 3B) The angled coupler 46 has a first end and a second end and is made of any suitable material such as plastic, PVC, steel or ABS. The second end of the angled coupler 46 is attached to the first end of a short piece of tubing 47 using a waterproof adhesive, or other suitable coupling device or material, to form a water tight seal. The short piece of tubing 47 can be made of any suitable material such as plastic, PVC, steel or ABS (not rubber). The second end of the short piece of tubing 47 is attached to the first end of a second angled coupler 48 of the same type and in the same manner as described above. The second end of the second angled coupler 48 is attached to the porous cup using a waterproof adhesive, or other suitable coupling device or material, to form a water tight seal. (see, FIG. 3B) The angled couplers 46 and 48 need to oriented so that they can trap water below the adapter inside the porous cup 38. The trapped water reduces the volume of air in the chamber 38 which allows the device to respond more quickly with less required water flow from the chamber 38 to the surrounding soil 11.

The third embodiment further consists of a coaxial inner guide tube 5 positioned within the outer guide tube 35. (see, FIG. 6A) The inner guide tube 5 is similar to the guide tube described in embodiment 1, but a stiffer material can be used if desired. The inner guide tube 5 has a first and second end. The first end of the inner guide tube 5 is attached to the first end of a transducer 17 using a waterproof adhesive. The transducer 17, stopper 10, transducer wire 19, and data logger 20 are the same type and perform the same function as described in embodiment 1. The perforated stopper mates with the complimentary inner surface of the adapter 45 or 8 to form a water tight seal. (see, FIGS. 3A and 3B)

When sealingly engaged with the adapter 34 or 8, the perforated stopper aperture 16 (see, FIGS. 3A and 3B) completes a pathway that allows water, air and pressure to travel between the porous cup 38 and the monitoring port of the transducer 17. This fluid communication allows the transducer to measure the pressure created by the water potential differential between the surrounding soil 11 and the water inside the porous cup 9.

The outer guide tube 33 and the inner guide tube 5 terminate with a joint 24 of the same type and function as described in Embodiment 1. (see, FIG. 6A)

The transducer wire 19 runs from the transducer 17, through the inner guide tube 36, up through the coupling device 12 terminating at a data logger 20. (see, FIG. 6A) The transducer wire 19 transmits the data from the transducer 17 to the data logger 20.

Method of Use

The method of operation for the third embodiment involves digging a borehole 35 into the side of the earthen material to be monitored. The porous cup 9, adapter 34 and outer guide tube 33 are then put into position. The space for the porous cup 9 should be located slightly lower than that of the outer guide tube 33. This difference in height helps keep the water in the porous cup from trickling out of porous cup 9 and down the guide tube 33. (see, FIG. 6A) Tap water is added to the porous cup using a syringe like device 25 that is attached to a pole 36. (see, FIG. 3B) The pole 36 and syringe device 25 (filled with water) are inserted into the outer guide tube 33. As the syringe mates with the adapter 34 the pole pushes on the backside of the syringe 25 and the syringe sprays water into the adapter until a sufficient amount has been added to fill the porous cup 9, adapter 34, and the lower part of the outer guide tube 33. (see, FIG. 6A and 6B) The inner guide tube 5 (with stopper 10 and transducer 17 attached) is then inserted through the coupling device 12 (with upper cap 14 off) into the outer guide 33 until the conical end of the perforated stopper 10 sealingly engages with the complimentary end of the conical seat of the adapter 34. A short length of the inner guide tube 5 should be left sticking out outer end of the coupling device 12. The upper cap 14 is screwed onto the upper part of the blank coupling, pressing against the inner guide tube 5 with sufficient force to maintain the seal between the perforated stopper and the adapter 34. The method of data recording is the same as described in embodiment 1.

Alternate Embodiments

The above embodiments can be further modified for use as a lysimeter (soil water sampler) like the one described in Hubbell et al, U.S. Pat. No. 5,915,476, which is hereby incorporated by reference in its entirety.

The lysimeter cylinder (moisture sampling device) is lowered into an outer guide tube of one of the above embodiments to the desired depth, where it can retrieve water samples for testing and other uses. The stopper (like the ones previously described) attached to the cylinder mates with the complimentary end of one of the adapters previously described to form a seal. A vacuum is then applied from the vacuum pump (through the vacuum tube attached to the vacuum pump on one end and the lysimeter cylinder on the other) and a partial vacuum in the device withdraws fluid from the surrounding geologic material over a period of time. The water passes through the porous cup, through the adapter into the sample reservoir of the cylinder. It should be noted that to get good samples, the water that was added to the monitoring apparatus for use as a tensiometer should be removed prior to using the apparatus as a lysimeter. Following this protocol will ensure that the samples recovered resemble the actual conditions of the surrounding soil.

The above embodiments can be further modified to include a portable tensiometer, as described in Hubbell, et al., U.S. Pat. No. 5,644,947, which is hereby incorporated by reference in its entirety. Use of the portable tensiometer eliminates the need for the porous cup, adapter, stopper and transducer as their functions are incorporated in the portable tensiometer itself.

A portable tensiometer (as described in Hubbell, et al., U.S. Pat. No. 5,655,947 or similar device) is lowered into an outer guide tube of one of the previous embodiments until the cup portion of the portable tensiometer is touching the surrounding soil, establishing a hydraulic connection. An inner guide tube and coupling device of the type used in the previous embodiments, may be used to maintain this hydraulic connection. After the portable tensiometer is in place, measurements can commence. When finished, the portable tensiometer can be removed and taken to another location.

What is claimed is:

1. A horizontal advanced tensiometer, comprising:
   a porous cup, having an interior surface and an exterior surface;
   a pressure transducer having a pressure monitoring end and an output end;
   an outer guide tube having a upper end and a lower end;
   an adapter having a first end and a second end, the adapter being coupled to the porous cup at the first end and coupled to the lower end of the outer guide tube at the second end, the adapter having an interior chamber, the chamber having an inner surface, the chamber housing the transducer, the interior surface of chamber near the second end of the adapter narrowing into a conically tapered seat;
   the porous cup and the chamber defining a passage permitting fluid communication between the pressure monitoring end of the transducer and the exterior surface of the porous cup;
   an inner guide tube having a first end and a second end, the inner guide tube positioned within the outer guide tube forming a coaxial relationship, the first end of the inner guide tube being coupled to the output end of the transducer;
   a threaded coupling device having a upper end and a lower end, the lower end being attached to the upper part of the outer guide tube, the coupling device having threads on the outside of its upper end;
   a data logger;
   a transducer wire positioned within the inner guide tube, one end of the wire being attached to the output end of the transducer, a second end of the wire being attached to the data logger.

2. A horizontal advanced tensiometer as set out in claim 1, wherein the upper end of the outer guide tube is straight, the middle section is curved and the lower end is straight.

3. A horizontal advanced tensiometer as set out in claim 1, further comprising:
   a gasket being coupled to the pressure monitoring end of the transducer, the gasket terminating in a conically tapered outer surface complementary to that of the tapered seat of the interior surface of the adapter chamber, the gasket having a central aperture that acts as a fluid connection between the porous cup and the pressure monitoring end of the transducer, wherein the conical end of the gasket sealingly engages with the conically tapered seat of the chamber to form a water tight seal.

4. A horizontal advanced tensiometer as set out in claim 1, further comprising:
   a cap for the threaded coupling device, the cap having an aperture large enough to allow the transducer wire to pass through but small enough to prevent the inner guide tube from passing through, the cap having threads that engage the threads on the upper end of the coupling device applying pressure on the inner guide tube relative to the degree of engagement.

5. A horizontal advanced tensiometer as set out in claim 1, wherein the joint between the porous cup and the chamber is water tight.

6. A horizontal advanced tensiometer as set out in claim 1, wherein the joint between the outer guide tube and the chamber is water tight.

7. A horizontal advanced tensiometer as set out in claim 1, wherein the exterior of the porous cup is in hydraulic contact with a surrounding soil environment.

8. A horizontal advanced tensiometer, comprising:
   a porous cup, having an interior surface and an exterior surface;
   a pressure transducer having a pressure monitoring end and a output end;

a horizontal guide tube having a straight end and an end with an elbow angled between 20°–160°;

a vertical guide tube having and upper end and a lower end;

a adapter having a first and second end, the first end of the adapter being coupled to end of the horizontal guide tube with the elbow, the second end of the adapter being coupled to the lower end of the vertical guide tube, the adapter having an interior chamber, the chamber having a inner surface, the chamber housing the transducer, the inner surface of chamber near the second end of the adapter narrowing into a conically tapered seat;

a data logger;

a transducer wire having a first and second end, the wire positioned within the vertical guide tube, the first end of the wire being attached to the output end of the transducer, the second end of the wire being attached to the data logger;

the porous cup, the horizontal guide tube and the chamber defining a channel permitting fluid communication between the pressure monitoring end of the transducer and the exterior of the porous cup.

9. A horizontal advanced tensiometer as set out in claim 8, further comprising:

a gasket being coupled to the pressure monitoring end of the transducer, terminating in a conically tapered outer surface complementary to that of the tapered seat of the adapter chamber, the gasket having a central aperture that acts as a fluid connection between the porous cup and the pressure monitoring end of the transducer, wherein the conical end of the gasket sealingly engages with the conically tapered seat of the chamber to form a water tight seal.

10. A horizontal advanced tensiometer as set out in claim 8, further comprising:

a gasket being coupled to the pressure monitoring end of the transducer, terminating in a conically tapered outer surface complementary to that of the tapered seat of the chamber, the gasket having a central aperture that acts as a fluid connection between the porous cup and the pressure monitoring end of the transducer, wherein the conical end of the gasket sealingly engages with the conically tapered seat of the adapter chamber to form a water tight seal, wherein the transducer is of sufficient weight that the gasket meets with the complimentary end of the chamber with sufficient force to form and maintain a seal.

11. A horizontal advanced tensiometer as set out in claim 8, wherein the joint between the horizontal guide tube and porous cup is water tight.

12. A horizontal advanced tensiometer as set out in claim 8, wherein the joint between the horizontal guide tube and chamber is water tight.

13. A horizontal advanced tensiometer as set out in claim 8, wherein the exterior surface of the porous cup is in hydraulic contact with a surrounding soil environment.

14. A horizontal advanced tensiometer, comprising:

a porous cup having an interior surface and an outer surface;

a horizontally oriented outer guide tube having a first end and a second end;

a pressure transducer having a pressure monitoring end and outlet end;

a coaxial inner guide tube with a first end and a second end, the inner guide tube positioned within the outer guide tube, the first end of the inner guide tube being coupled to the output end of the transducer;

an adapter having a first end and a second end, the first end of the adapter having an upper aperture and the second end of the adapter having a lower aperture, the upper aperture being coupled to the first end of the outer guide tube and lower aperture being coupled to the porous cup, the adapter having a chamber, the chamber having an inner surface, the chamber housing the transducer;

the inner surface of the chamber defining a fluid channel formed through the adapter between the upper and lower apertures, the interior surface of the chamber near the first end of the adapter narrowing into a conically tapered seat;

the interior of the porous cup and the interior of the chamber defining a channel permitting fluid communication between the pressure monitoring end of the transducer and the exterior surface of the porous cup;

a threaded coupling device having a first end and a second end, the first end being attached to the second end of the outer guide tube, the coupling device having threads on the outside of its second end.

15. A horizontal advanced tensiometer as set out in claim 14, further comprising:

a gasket being coupled to the pressure monitoring end of the transducer, the gasket terminating in a conically tapered outer surface complementary to that of the tapered seat of the chamber, the gasket having a central aperture that acts as a fluid connection between the porous cup and the pressure monitoring end of the transducer and wherein the conical end of the gasket sealingly engages with the conically tapered seat of the chamber to form a water tight seal.

16. A horizontal advanced tensiometer as set out in claim 14, further comprising:

a cap for the threaded coupling device, the cap having an aperture large enough to allow the transducer wire to pass through but small enough to prevent the inner guide tube from passing through, the cap having threads that engage with threads on the upper end of the coupling device applying pressure on the inner guide tube relative to the degree of engagement.

17. A horizontal advanced tensiometer as set out in claim 14, further comprising:

a means for trapping fluid inside the porous cup at a height lower than that of the adapter.

18. A horizontal advanced tensiometer as set out in claim 14, wherein the joint between the horizontal guide tube and chamber is water tight.

19. A horizontal advanced tensiometer as set out in claim 14, wherein the joint between the porous cup and the chamber is water tight.

20. A horizontal advanced tensiometer as set out in claim 14, wherein the exterior of the porous cup is in contact with a surrounding soil environment.

21. A horizontal advanced tensiometer, comprising:

an outer guide tube having and upper end and a lower end, wherein the upper end of the outer guide tube is straight, the middle section is curved and the lower end is straight;

an inner guide tube a first end and a second end, the inner guide tube positioned within the outer guide tube forming a coaxial relationship, the first end of the inner guide tube being coupled to the output end of the transducer;

a portable tensiometer positioned within the outer guide tube and in hydraulic contact with the surrounding soil;

a threaded coupling device having an upper end and a lower end, the lower end being attached to the upper part of the outer guide tube, the coupling device having threads on the outside of its upper end;

a cap for the threaded coupling device, the cap having threads that engage the threads on the upper end of the coupling device applying pressure on the inner guide tube relative to the degree of engagement.

* * * * *